(12) United States Patent
Karahalios

(10) Patent No.: US 7,238,205 B2
(45) Date of Patent: Jul. 3, 2007

(54) UNIVERSAL INTERFERENCE CLEAT

(75) Inventor: Dean G. Karahalios, Indianapolis, IN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 168 days.

(21) Appl. No.: 10/758,365

(22) Filed: Jan. 15, 2004

(65) Prior Publication Data

US 2005/0159814 A1    Jul. 21, 2005

(51) Int. Cl.
*A61F 2/44* (2006.01)
(52) U.S. Cl. .................................. 623/17.11
(58) Field of Classification Search ........ 623/17.11–16
See application file for complete search history.

(56) References Cited

U.S. PATENT DOCUMENTS

| | | | |
|---|---|---|---|
| 4,401,112 A | 8/1983 | Rezaian | |
| 4,657,550 A | 4/1987 | Daher | |
| 4,820,305 A | 4/1989 | Harms et al. | |
| 4,932,975 A | 6/1990 | Main et al. | |
| 5,026,373 A | 6/1991 | Ray et al. | |
| 5,062,850 A | 11/1991 | MacMillan et al. | |
| 5,336,223 A | 8/1994 | Rogers | |
| 5,571,190 A | 11/1996 | Ulrich et al. | |
| 5,571,192 A | 11/1996 | Schonhoffer | |
| 5,702,451 A | 12/1997 | Biedermann et al. | |
| 5,702,453 A * | 12/1997 | Rabbe et al. ............ | 623/17.16 |
| 5,702,455 A | 12/1997 | Saggar | |
| 5,989,290 A * | 11/1999 | Biedermann et al. .... | 623/17.11 |
| 6,015,436 A | 1/2000 | Schonhoffer | |
| 6,086,613 A | 7/2000 | Camino et al. | |
| 6,190,413 B1 | 2/2001 | Sutcliffe | |
| 6,193,755 B1 | 2/2001 | Metz-Stavenhagen et al. | |
| 6,193,756 B1 * | 2/2001 | Studer et al. ............ | 623/17.15 |
| 6,616,695 B1 * | 9/2003 | Crozet et al. ............ | 623/17.11 |
| 7,156,874 B2 * | 1/2007 | Paponneau et al. ...... | 623/17.11 |
| 2003/0181980 A1 | 9/2003 | Berry et al. | |
| 2003/0191531 A1 * | 10/2003 | Berry et al. ............ | 623/17.11 |
| 2004/0186569 A1 * | 9/2004 | Berry ..................... | 623/17.11 |
| 2005/0090898 A1 * | 4/2005 | Berry et al. ............ | 623/17.11 |
| 2005/0209697 A1 * | 9/2005 | Paponneau et al. ...... | 623/17.15 |

FOREIGN PATENT DOCUMENTS

| | | |
|---|---|---|
| DE | 195 09 317 A | 9/1996 |
| FR | 2 636 227 | 3/1990 |
| WO | WO 00/45751 | 8/2000 |
| WO | WO 02/071986 | 9/2002 |
| WO | WO 2004/089256 | 10/2004 |

OTHER PUBLICATIONS

Patent Cooperation Treaty—European Patent Office, "Notification of Transmittal of The International Search Report and The Written Opinion of the International Searching Authority, or the Declaration," May 19, 2005, 15 pages.

* cited by examiner

*Primary Examiner*—Eduardo C. Robert
*Assistant Examiner*—Annette Reimers
(74) *Attorney, Agent, or Firm*—Haynes and Boone, LLP

(57) ABSTRACT

A vertebral implant comprises a tubular body sized to fit between two vertebral endplates and a pair of ring-shaped cleat assemblies. Each cleat assembly comprises an outer end wall, an inner end wall, and a side wall which defines a hollow bore. One or more spikes extend from each outer end wall, and each hollow bore is sized to fit over an end of the tubular body and slidably pass from the end along at least a portion of the length of the tubular body.

22 Claims, 4 Drawing Sheets

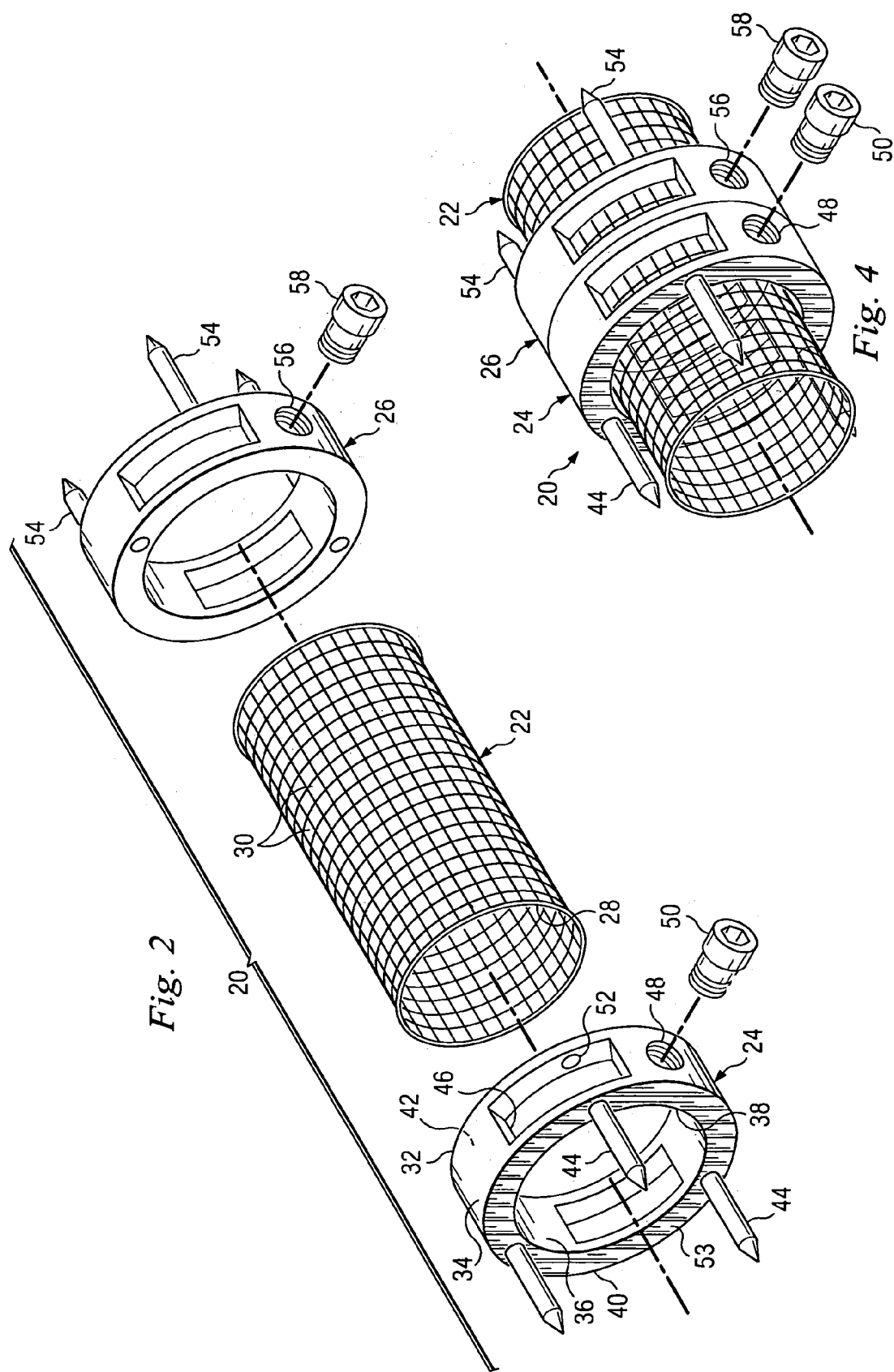

US 7,238,205 B2

UNIVERSAL INTERFERENCE CLEAT

FIELD OF THE INVENTION

The present invention relates generally to an implant for replacement of one or more vertebral bodies and their adjacent discs, and more particularly, to a vertebral implant assembly having cleats for stabilizing the assembly.

BACKGROUND

A variety of spinal injuries and deformities can occur due to trauma, disease, or congenital effects. These injuries and diseases can, ultimately, result in the destruction of one or more vertebral bodies and lead to a vertebrectomy in which the one or more damaged vertebral bodies and their adjacent discs are excised. Reconstruction of the spine following the vertebrectomy can present a number of challenges for the surgeon.

One surgical concern is securely interposing a vertebral implant between the remaining rostral and caudal vertebral bodies to ensure that the implant can resist axial, torsional, and shear loading without causing anterior displacement ("kick-out") or posterior retropulsion of the implant and any associated graft material. Existing vertebral implants which attempt to minimize these methods of failure can often result in other undesirable consequences such as instrumentation pull-out, graft or implant subsidence, graft dislodgment, or erosion of nearby vascular and soft tissue structures due to high profile design.

Therefore, a vertebral implant assembly is needed that resists kick out and retropulsion without injuring proximate bone, vascular, or soft tissue structures and also without significantly lengthening or complicating the surgical procedure.

BRIEF DESCRIPTION OF THE DRAWINGS

FIG. 2 is an exploded perspective view of a vertebral implant assembly according to one embodiment of the present invention.

FIG. 4 is a perspective view of a vertebral implant assembly in an unengaged position.

DETAILED DESCRIPTION

Figure 1:
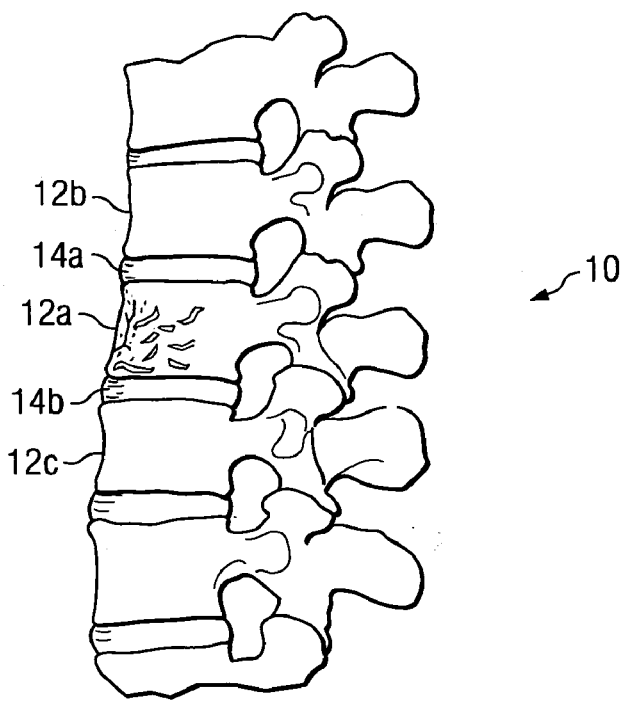
FIG. 1 is an perspective view of a destroyed vertebral body within a vertebral column.

For the purposes of promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Referring first to FIG. 1, the reference numeral 10 refers to a vertebral column with a damaged vertebra 12a extending between two intact vertebrae 12b and 12c. An intervertebral disc 14a extends between vertebrae 12a and 12b, and an intervertebral disc 14b extends between vertebrae 12a and 12c. In a typical surgical excision, the vertebra 12a is removed together with discs 14a and 14b creating a void between the two intact vertebra 12b and 12c. This procedure may be performed using an anterior, anterolateral, or other approach known to one skilled in the art. A vertebral implant assembly according to an embodiment of the present invention is then provided to fill the void between the two intact vertebrae 12b and 12c. Although the embodiment to be described is premised upon the removal of a single vertebra, it is understood that a different embodiment of the present invention may be inserted in an intervertebral disc space without the removal of a vertebrae when required by the surgical procedure. In still another embodiment, the present invention may be used in a vertebral column reconstruction following a vertebrectomy removing two or more diseased or damaged vertebrae and their adjacent discs.

Referring now to FIG. 2, a vertebral implant assembly according to an embodiment of the present invention is referred to, in general, by the reference numeral 20 and includes tubular body 22 connected between two cleat assemblies 24 and 26 in a manner to be described. The tubular body 22 defines a hollow bore 28 therethrough which is configured to receive bone osteogenetic material (not shown). To fully exploit the osteogenetic material and promote healing and bone restoration in the aftermath of vertebral or disc surgery, the tubular body 22 can be provided with a plurality of openings 30 that permit bone and tissue ingrowth and vascularization. The body 22 may be provided in a variety of heights or may be trimmed to fit within the gap formed by the vertebral ablation to avoid damaging the weak bone of the adjacent intact vertebrae after implantation.

In one embodiment, a surgical mesh tube or "cage," which is known in the art, can serve as the tubular body 22. One example of such a cage is disclosed in U.S. Pat. Nos. 5,897,556 and 6,149,651 to Drewry, et al. ("the Drewry patents") which are incorporated herein by reference. As described in the Drewry patents, a tubular body may comprise angled, intersecting elongate bars which form a plurality of triangular apertures. Also as described in the Drewry patents, the tubular body may have a non-circular cross section and instead be shaped to more closely match the profile of the adjacent intact vertebrae, so that when installed, the tubular body can be as unobtrusive as possible.

The cleat assembly 24 can include a ring-shaped member 32 having an exterior side wall 34 and interior side wall 36 which defines a bore 38 through which the tubular body 22 can pass, such as by sliding. The interior side wall 36 may be smooth to promote the slidable passage of the tubular body 22. The member 32 can further include an outer end wall 40 and an inner end wall 42 extending between the exterior side wall 34 and interior side wall 36, the outer end wall 40 having a plurality of spikes 44 configured to penetrate the endplate of the adjacent intact vertebrae to maintain the position of the cleat assembly 24 in situ.

To promote bone ingrowth and vascularization in and around cleat assembly 24, one or more apertures 46 can be provided through the exterior side wall 34 and the interior side wall 36 and into communication with the bore 38. After installation, these apertures 46 can be packed with graft material to accelerate the healing process. Additionally, to fix the cleat assembly 24 to the tubular body 22 after installation, one or more threaded apertures 48 can be provided through the side walls 34 and 36 of the member 32 in communication with the bore 38 with each aperture 48 being adapted to receive an attachment mechanism 50, which can be, for example, a flat end machine type screw. Other examples include a pre-attached pin, a rivet, and/or a staple.

To facilitate installation, the inner end wall 42 of the cleat assembly 24 may be provided with a plurality of alignment positions 52 which can be configured to mate with corresponding pegs on an installation tool (not shown) to permit rotational and axial placement of the cleat assembly 24. Depending where the alignment positions 52 are located along the inner end wall 42, the alignment positions 52 may be configured either as recessed areas in the inner end wall 42 or as openings that extend through the inner end wall 42 and into communication with the apertures 46. In another alternative, the alignment positions 52 may project outward from the inner end wall 42 to mate with corresponding recessed areas on an installation tool (not shown). The outer end wall 40 can comprise furrows 53 or other textures to reduce motion and promote a secure interface between the cleat assembly 24 after the spikes 44 of the cleat assembly have been embedded in the endplate of the adjacent intact vertebra.

In alternative embodiments, the configuration of the cleat assembly 24 can be modified to accommodate a wide variety of patient anatomies and surgical applications while still providing a secure and stable engagement with the adjacent intact vertebrae. To correspond to the cervical, thoracic, or lumbar regions of the vertebral column or to most closely match the anatomy of a particular patient, the member 32 can be fabricated in a wide assortment of diameters. Further, the interior side wall 36 may be sized to allow the tubular body 22, having a predetermined diameter which can range for example from 13 mm through 25 mm, to slidably pass through the member 32. Although FIG. 2 depicts the ring-shaped member 32 as generally cylindrical, to provide an unobtrusive alignment with the adjacent intact vertebrae, the exterior side wall 34 and/or the interior side wall 36 can be contoured to more closely correspond to the shape of the adjacent intact vertebrae, resulting in a low profile installation.

Figure 3A:
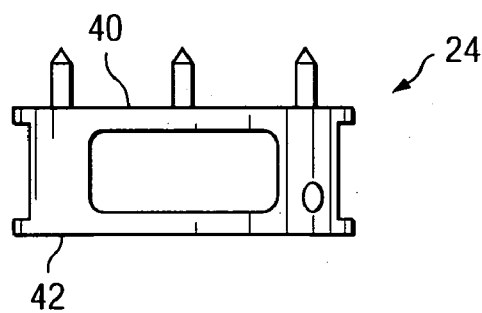
FIG. 3a is a perspective view of a cleat assembly according to a first embodiment of the present invention.
Figure 3B:
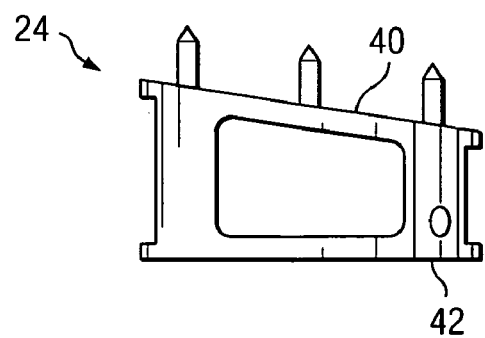
FIG. 3b is a perspective view of a cleat assembly according to a second embodiment of the present invention.

Referring now to FIG. 3a, the cleat assembly 24 can have the outer end wall 40 in substantially parallel alignment with inner end wall 42. Alternatively, as shown in FIG. 3b, the cleat assembly 24 can have end walls 40 and 42 which may be angled with respect to each other to accommodate a variety of lordotic and kyphotic angles. The angled end walls can provide a secure and stable installation that most closely matches the alignment required for a particular patient. For example, the cleat assembly 24 may have lordotic angles of 4, 8 or 15 degrees.

Referring again to FIG. 2, the cleat assembly 26 can include one or more spikes 54 and one or more threaded apertures 56 having a corresponding set screw 58. The spikes 54, apertures 56, and set screw 58 can be identical to the spikes 44, apertures 48, and set screw 50 described above for cleat assembly 24. Other features of cleat assembly 26 can be the same as the cleat assembly 24 and therefore, will not be described in detail. It should be noted, however, that the cleat assembly 24 may not, necessarily, be identical to the cleat assembly 26. For example, cleat assembly 24 may comprise substantially parallel end walls as shown in FIG. 3a, whereas cleat assembly 26 may be identical to cleat assembly 24 shown in FIG. 3b, comprising end walls angled with respect to each other.

The tubular body 22 and the cleat assemblies 24 and 26 may be formed of or include a biocompatible material. The material may be strong enough to withstand the application of external compressive, axial, torsional, and bending loads, as well as strong enough to provide support for the adjacent intact vertebrae. The devices may be formed entirely of titanium, however other biocompatible materials may be used such as a surgical grade stainless steel, a porous tantalum material such as HEDROCEL® provided by Implex Corporation of Allendale, N.J., or a radiolucent polymer material, such as polyether ether ketone (PEEK™) provided by Victrex PLC of the United Kingdom. The components 22, 24, and 26 of vertebral implant assembly 20 may all be formed from the same material or, alternatively, may be fabricated from different but compatible materials.

Referring now to FIG. 4, the components of FIG. 2 may be preliminarily assembled to permit implantation of the vertebral implant assembly 20 into the void created in the vertebral column by a vertebral ablation. For instance, once the tubular body 22 has been selected and/or trimmed to fit within the gap between the intact vertebrae (as discussed with reference to FIG. 1), the cleat assembly 24 can be placed over an end of the tubular body 22 with spikes 44 extending toward that end of the body. The cleat assembly 26 can be placed over the other end of the tubular body 22 with spikes 54 extending toward that other end of the body and in the direction opposite the spikes 44. To permit installation without damaging the weak bone of the adjacent endplates, the cleat assemblies can be slidably positioned along the tubular body 22 such that the spikes do not project past the ends of the tubular body.

The tubular body 22 can then be packed with a suitable osteogenetic material (not shown), including autograft, allograft, xenograft, demineralized bone, synthetic and natural bone graft substitutes, such as bioceramics and polymers, and osteoinductive factors. It is understood that the osteogenetic graft material can be packed at any time prior to or during the installation of the vertebral implant assembly 20, and can even be packed after installation by inserting the graft through the openings 30 in the tubular body 22.

Figure 5:
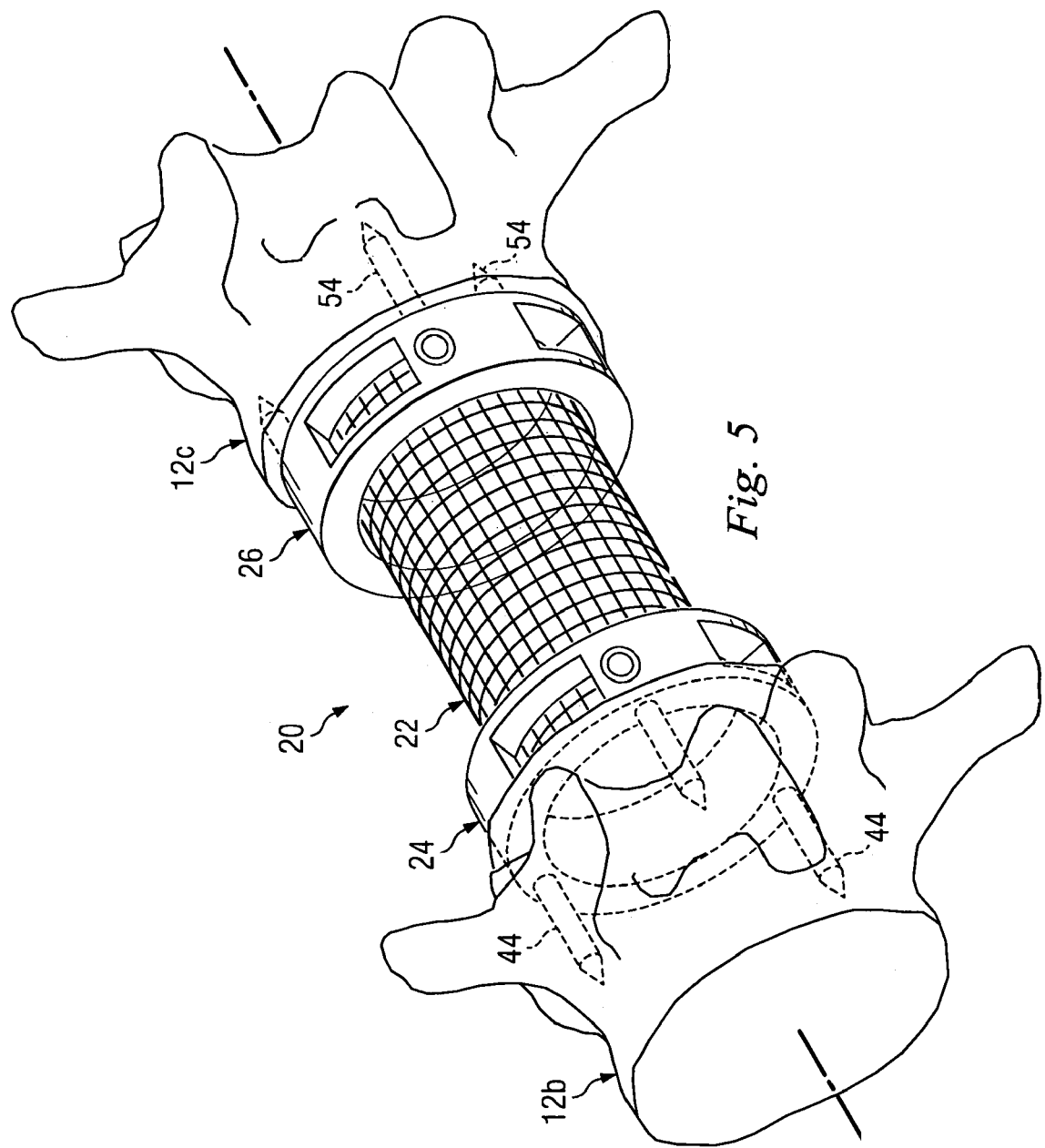
FIG. 5 is a perspective view of a vertebral implant assembly disposed between intact vertebrae.

Referring now to FIG. 5, the configuration of FIG. 4 can be surgically inserted into the void created by the surgical excision of vertebra 12a (in FIG. 1) with spikes 44 extending toward intact vertebra 12b and spikes 54 extending toward intact vertebra 12c. The cleat assemblies 24 and 26 can be advanced along the tubular body 22 toward the endplates of the intact vertebrae until the spikes are embedded into the endplates.

Depending upon the surgical approach and the amount of surgical exposure, embedding the cleat assemblies into the vertebral endplates may be achieved using one or more devices known in the art. In one example, the cleat assemblies may be installed using an impactor having a forked or variable C-shaped head which can accommodate a variety of cleat assembly diameters. Pegs on the impactor head can mate with the alignment positions 52 in the outer end wall 40 of the cleat assembly 24 to rotationally and axially position the cleat assembly and to grip the cleat assembly while a mallet is used to strike the impactor, embedding the spikes into the adjacent vertebral endplate. The process may be repeated for cleat assembly 26.

Another device that can be used to install the cleat assemblies is a distractor which can be interposed between the two cleat assemblies to force them away from each other and into the adjacent vertebral endplates. After the spikes of the cleat assemblies are embedded using, for example the distractor or the impactor, the distractor also may be used create a desirable spacing between the rostral and caudal intact vertebrae, allowing for the surgical restoration of sagittal plane balance. Still another device for seating the cleat assemblies is a compressor which, when anchored to a relatively stationary structure, can be used to pull the spikes into the endplates of the adjacent vertebrae. These devices or others known in the art can be used alone or in concert to install the cleat assemblies and create the desired spacing between the adjacent vertebrae.

After the cleat assemblies 24 and 26 are installed and properly spaced, the attachment mechanism 50 (a set screw in the present example) can be inserted into the aperture 48 of cleat assembly 24 and rotated until at least a portion emerges through the interior side wall 36. In some embodiments, the set screw 50 may be pre-attached. The set screw 50 can further pass through the mesh of the tubular body 22 to affix the tubular body 22 to the cleat assembly 24. Alternatively, the set screw can exert pressure on the surface of the tubular body 22 to affix the body 22 to the cleat assembly 24. The cleat assembly 26 can be affixed to the tubular body 22 in a manner identical to that described for assembly 24. After the vertebral body replacement assembly 20 is installed, additional osteogenetic material may be packed into the cleat assembly 24 through the apertures 42 to promote healing and bone growth. The assembly 26 can be similarly packed with osteogenetic material.

As compared to other anterior stabilizing techniques, the installation of this vertebral implant assembly 20 can be relatively simple and can have a shortened procedure duration relative to surgical procedures that require implantation of other hardware or the preparation of mortises. Additionally, the vertebral implant assembly 20 can be installed to complement and not interfere with other implanted stabilizing devices such as screw and plate, screw and rod, and pedicle screw systems. Once installed, the implant 20 can have a very low profile, reducing the risk of erosion of vascular structures.

The vertebral body replacement assembly 20 installed as described can withstand torsional, axial, and shear loads, reducing the risk of anterior displacement or posterior retropulsion and thus minimizing the development of neurologic deficits in the patient and the need for additional surgery. Furthermore, this installation can resist subsidence ("telescoping") of the tubular body or the biologic strut into the relatively weak bone of the adjacent vertebral endplates which occurs commonly with conventional mortising techniques. This resistance to subsidence can be due to both the embedded spikes and the wider surface area of the end walls which distribute loads over a greater area of the adjacent intact vertebrae end. Because the cleat assemblies are not positioned within the hollow bore of the tubular body but rather are externally fixed to the body, the disclosed configuration provides the further advantage of permitting increased contact between the osteogenetic material located within the tubular body and the endplates of the adjacent vertebrae to promote bone growth.

An alternative installation method may prove advantageous for some applications, for example, the components of the vertebral implant assembly 20 may not be preliminarily assembled. Rather, the spikes 44 and 54 of cleat assemblies 24 and 26, respectively, may be driven into the intact vertebrae 12b and 12c (FIG. 1) before the tubular body 22 is passed between the cleat assemblies 24 and 26. The tubular body 22 may then be packed with osteogenetic material and slidably positioned into the space between the cleat assemblies 24 and 26. The set screws 50 & 58 can then be installed as described above.

Figure 6:
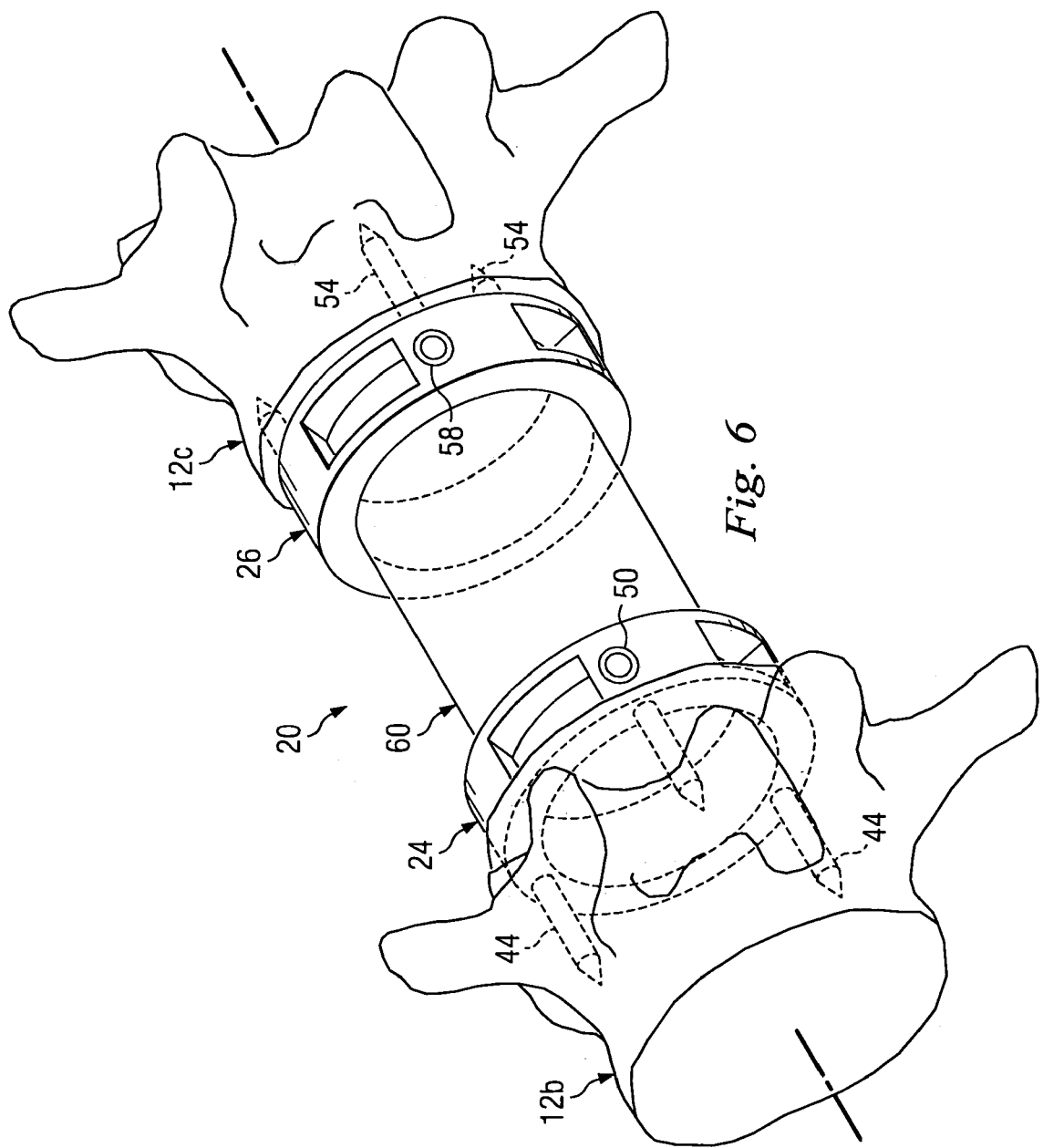
FIG. 6 is a perspective view of a vertebral implant assembly, comprising a biologic strut, disposed between intact vertebrae.

Referring now to FIG. 6, in another alternative embodiment, the tubular body 22 can be replaced with a biologic strut graft 60 to form a vertebral implant assembly 62. The strut may be allograft or autograft material and the graft may be taken from a fibula, a humerus, or any other suitable source known in the art. In this embodiment, the endplates 24 and 26 are placed over a biologic strut graft 60 which is sized to fit between the endplates of the adjacent intact vertebrae. The vertebral implant assembly 62 can then be installed in a manner similar to the method described for vertebral implant assembly 20. In this embodiment, however, set screws 50 & 58 may be of a type that can be threaded into the biologic strut graft 56. For example, a pointed screw may be appropriate.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims. In the claims, means-plus-function clauses are intended to cover the structures described herein as performing the recited function and not only structural equivalents, but also equivalent structures.

What is claimed is:

1. A vertebral implant for interposition between two vertebral endplates comprising:
   a tubular body sized to fit between the two vertebral endplates;
   a pair of ring-shaped cleat assemblies, each cleat assembly comprising an outer end wall, an inner end wall, and a side wall which defines a hollow bore,
   wherein one or more spikes extend from each outer end wall, and wherein each hollow bore is sized to fit over an end of the tubular body and is configured to slidably pass from the end along at least a portion of the length of the tubular body directly in an axial direction, wherein prior to interposition between the two vertebral endplates, the tubular body is slidably passed through the hollow bores in each of the cleat assemblies and wherein the spikes on each outer end wall are directed away from each other and extend toward opposite ends of the tubular body without extending past the opposite ends of the tubular body.

2. The vertebral implant of claim 1 further comprising an attachment assembly for attaching the tubular body to the cleat assemblies, the attachment assembly comprising:
   one or more apertures extending through the side walls of each of the cleat assemblies;
   an attachment member extendable through one of the one or more apertures into contact with the tubular body.

3. The vertebral implant of claim 2 wherein the one or more apertures is threaded and the attachment member is a set screw.

4. The vertebral implant of claim 1 wherein one or more openings extend through the side walls of each of the cleat assemblies, the openings sized to permit graft material entry into the hollow bore.

5. The vertebral implant of claim 1 wherein the inner end wall of each of the cleat assemblies is provided with one or more alignment positions for aligning and positioning the cleat assemblies.

6. The vertebral implant of claim 1 wherein for at least one of the cleat assemblies, the outer end wall is angled with respect to the inner end wall.

7. The vertebral implant of claim 6 wherein the angle between the outer end wall and the inner end wall is between 4 and 15 degrees.

8. The vertebral implant of claim 1 wherein the end walls of the cleat assemblies are furrowed.

9. The vertebral implant of claim 1 wherein the side wall of each cleat assembly is smooth.

10. The vertebral implant of claim 1 wherein the hollow bore has a diameter between 13 mm and 25 mm.

11. A vertebral implant for interposition between two vertebral endplates comprising:
   a biologic strut sized to fit between the two vertebral endplates;
   a pair of ring-shaped cleat assemblies, each cleat assembly comprising an outer end wall, an inner end wall, and a sidewall which defines a hollow bore, wherein one or more spikes extend from each outer end wall, and wherein each hollow bore is sized to fit over an end of the biologic strut and is configured to slidably pass from the end along at least a portion of the length of the biologic strut directly in an axial direction, wherein prior to interposition between the two vertebral endplates, the biological strut is slidably passed through the hollow bores in each of the cleat assemblies and wherein the spikes on each outer end wall are directed away from each other and extend toward opposite ends of the biologic strut without extending past the opposite ends of the biologic strut.

12. The vertebral implant of claim 11 further including at least one threaded aperture through each sidewall and a set screw extendable through each aperture for fixing the biologic strut to the cleat assemblies.

13. The vertebral implant of claim 11 wherein the set screws are extended through each aperture after a distractive force separates the cleat assemblies to achieve a desired vertebral alignment.

14. A vertebral implant system for interposition in a variable space between two vertebral endplates to create a desired vertebral alignment, the implant system comprising:
   a tubular body having a first opposite end and a second opposite end, the tubular body sized to span at least a portion of the space between the vertebral endplates;
   a first cleat assembly comprising a first spiked end wall for attaching the first cleat assembly to one of the vertebral endplates and a first side wall defining a first hollow bore sized so that the first opposite end slidably passes through the first cleat assembly directly in an axial direction;
   a second cleat assembly comprising a second spiked end wall for attaching the second cleat assembly to the other vertebral endplate and a second side wall defining second hollow bore sized so that the second opposite end slidably passes through the second cleat assembly, wherein the first cleat assembly is slidably passed over the first opposite end and the second cleat assembly is slidably passed over the second opposite end with the first spiked end wall directed toward the first opposite end and the second spiked end wall directed toward the second opposite end and wherein the spiked end walls do not extend beyond the first and second opposite ends.

15. The system of claim 14 further comprising an attachment system for fixing the first and second cleat assemblies to the tubular body after the first and second cleat assemblies have been attached to the vertebral endplates.

16. The system of claim 15 wherein the attachment system comprises at least one threaded aperture in each of the first and second side walls and a set screw extendable through each of the threaded apertures.

17. The system of claim 16 wherein the set screws are extended through each of the threaded apertures after a distracting force varies the space between vertebral endplates to create the desired vertebral alignment.

18. The system of claim 14 wherein one or more openings, sized to permit graft material entry into the first hollow bore, extend through the first sidewall.

19. A method for inserting a vertebral implant between two vertebral endplates, wherein the vertebral implant comprises a pair of cleat assemblies and a tubular body, the method comprising:
   sliding the cleat assemblies over the tubular body;
   inserting the vertebral implant between the vertebral endplates;
   interposing a distracting device between the cleat assemblies;
   applying a distracting force with the distracting device to move at least one of the cleat assemblies into engagement with at least one of the vertebral endplates.

20. The method of claim 19 further comprising:
   responsive to the distractive force, expanding a space between the two vertebral endplates; and
   attaching each cleat assembly to the tubular body with an attachment mechanism to maintain the expanded spacing.

21. The method of claim 20 wherein the attachment mechanism is a set screw.

22. The method of claim 19 wherein during the insertion of the vertebral implant, the cleat assemblies do not extend past the ends of the tubular body.

* * * * *